(12) United States Patent
Choi et al.

(10) Patent No.: US 9,968,411 B2
(45) Date of Patent: May 15, 2018

(54) MICRO-ROBOT COUPLED TO CATHETER

(71) Applicant: Daegu Gyeongbuk Institute of Science and Technology, Daegu (KR)

(72) Inventors: Hong Soo Choi, Daegu (KR); Sang Hun Jeon, Hadong-gun (KR); Jeong Hun Lee, Buyeo-gun (KR); Seung Min Lee, Gumi-si (KR); Sang Won Kim, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 169 days.

(21) Appl. No.: 15/044,517

(22) Filed: Feb. 16, 2016

(65) Prior Publication Data
US 2016/0235491 A1    Aug. 18, 2016

(30) Foreign Application Priority Data

Feb. 16, 2015  (KR) .................. 10-2015-0023276
Feb. 17, 2015  (KR) .................. 10-2015-0023999
Oct. 13, 2015  (KR) .................. 10-2015-0142724
Feb. 16, 2016  (KR) .................. 10-2016-0017540

(51) Int. Cl.
*A61B 34/30*   (2016.01)
*A61B 34/00*   (2016.01)
(Continued)

(52) U.S. Cl.
CPC .............. *A61B 34/30* (2016.02); *A61B 34/73* (2016.02); *A61N 1/00* (2013.01); *A61B 2018/00208* (2013.01); *A61B 2034/301* (2016.02); *A61B 2034/303* (2016.02); *A61B 2090/378* (2016.02); *A61N 1/05* (2013.01); *A61N 1/36* (2013.01)

(58) Field of Classification Search
CPC ... A61B 34/30; A61B 34/73; A61B 2034/303; A61B 2090/378; A61B 2034/301; A61B 2018/00208; A61B 2018/00202; A61B 17/320758; A61M 25/00
See application file for complete search history.

(56) References Cited

U.S. PATENT DOCUMENTS

| | | | |
|---|---|---|---|
| 3,674,014 | A | 7/1972 | Tillander |
| 8,328,790 | B2 | 12/2012 | Chesnin |

(Continued)

FOREIGN PATENT DOCUMENTS

| | | | |
|---|---|---|---|
| JP | 2004016504 A | * | 1/2004 |
| JP | 2004-215992 A | | 8/2004 |

(Continued)

OTHER PUBLICATIONS

Machine Translation of JP 2004016504 A (Jan. 2004).*
(Continued)

*Primary Examiner* — Katrina Stransky
(74) *Attorney, Agent, or Firm* — Sughrue Mion, PLLC

(57) ABSTRACT

Provided is a micro-robot which is integratedly or detachably coupled to one end of a catheter or a guidewire for performing a medical operation using the catheter. Steering and drilling are independently performed by using a catheter thinner in thickness than a related art catheter. The a micro-robot is smoothly inserted into a lesion part and removes a risk of injury and infection in an opening operation through precise steering.

12 Claims, 12 Drawing Sheets

(51) Int. Cl.
*A61N 1/00* (2006.01)
*A61B 18/00* (2006.01)
*A61B 90/00* (2016.01)
*A61N 1/05* (2006.01)
*A61N 1/36* (2006.01)

(56) References Cited

U.S. PATENT DOCUMENTS

| | | |
|---|---|---|
| 8,715,280 B2 | 5/2014 | Tegg |
| 2009/0306651 A1 | 12/2009 | Schneider |
| 2012/0035539 A1 | 2/2012 | Tegg |
| 2017/0071622 A1 | 3/2017 | Jang et al. |

FOREIGN PATENT DOCUMENTS

| | | |
|---|---|---|
| KR | 10-0351320 B1 | 9/2002 |
| KR | 10-2009-0122648 A | 12/2009 |
| KR | 10-2010-0107638 A | 10/2010 |
| KR | 101217767 B1 | 1/2013 |
| KR | 10-1394195 B1 | 5/2014 |
| KR | 101458938 B1 | 11/2014 |
| KR | 10-1471526 B1 | 12/2014 |
| WO | 2009/145405 A1 | 12/2009 |

OTHER PUBLICATIONS

Korean Intellectual Property Office; Communication dated Nov. 9, 2016 in counterpart application No. 10-2015-0023999.
Korean Intellectual Property Office, Communication dated May 2, 2016 issued in counterpart Application No. 10-2015-0023999.
Korean Intellectual Property Office, Communication dated Jul. 27, 2017, issued in counterpart Korean Application No. 10-2016-0017540.
Korean Intellectual Property Office; Communication dated Aug. 23, 2017 in counterpart application No. 10-2015-0023999.
Korean Intellectual Property Office, Communication dated Mar. 27, 2018 in counterpart application No. 10-2016-0017540 with English translation.

\* cited by examiner

US 9,968,411 B2

MICRO-ROBOT COUPLED TO CATHETER

CROSS-REFERENCE TO RELATED APPLICATIONS

This application claims priority under 35 U.S.C. § 119 to Korean Patent Application No. 10-2015-0023276, filed on Feb. 16, 2015, No. 10-2015-0023999, filed on Feb. 17, 2015, No. 10-2015-0142724, filed on Oct. 13, 2015, and No. 10-2016-0017540, filed on Feb. 16, 2016, the disclosure of which is incorporated herein by reference in its entirety.

TECHNICAL FIELD

The present invention relates to a micro-robot, and more particularly, to a micro-robot which is integratedly or detachably coupled to one end of a catheter for performing a medical operation using the catheter.

BACKGROUND

Generally, catheters are applied to percutaneous transluminal angioplasty (PTA) and percutaneous transluminal coronary angioplasty (PTCA) for extension-treating blockage parts or stenosis parts such as a coronary artery, a limb artery, a renal artery, a peripheral vessel, and/or the like.

In the PTA, a guiding catheter is inserted through a femoral artery, a front end of the guiding catheter is disposed in an inlet of a coronary artery through a main artery, a guidewire passes through an occlusion part and a lesion of a blockage part or a stenosis part such as a coronary artery or the like, the catheter is inserted along the guidewire and matches the lesion, and the catheter is extended by supplying a contrast agent to the catheter. After an extensive treatment is performed for the lesion, the catheter is depressurized and contracted and then is discharged to outside a human body.

Recently, a treatment applicable to a lesion blood vessel part where a degree of stenosis or a degree of flection is high and a level of difficulty is very high is being attempted by combing a robot surgery with a catheter.

In a for controlling a magnetic field, since a wire is bent by using a magnetic torque, a magnetic material having a very large size should be mounted on a distal end of a catheter, and an intensity (for example, 800 mT) of an external magnetic field which has a very high level in correspondence with the magnetic material is needed.

Therefore, in the related art, a size of a distal end of the catheter is inevitably enlarged, and for this reason, the related art catheter-attachable micro-robot is not suitable for a guidewire or a catheter having a small diameter.

Moreover, a related art catheter is applied to the field where a lesion part is opened and then a stent is performed, but is not smoothly inserted into the lesion part. In a case where a medical operation (for example, cardiovascular obstruction opening treatment or the like) is performed, since it is difficult to precisely steer a catheter, a risk of injury and infection is high in adsorbed hemoclasis and inosculation.

SUMMARY

Accordingly, the present invention provides a micro-robot coupled to a catheter or a guidewire, in which steering and drilling are independently performed by using a catheter thinner in thickness than a related art catheter.

The present invention also provides a micro-robot coupled to a catheter or a guidewire, which is smoothly inserted into a lesion part and removes a risk of injury and infection in an opening operation through precise steering.

In one general aspect, the catheter-attachable micro-robot according to an embodiment of the present invention may be applied to and used along with a magnetic field emitter that is disposed in plurality outside a patient, a magnetic field control system that controls an intensity of an external steering magnetic field or an external rotating magnetic field to provide the intensity-controlled external steering magnetic field or external rotating magnetic field to the magnetic field emitter, and a catheter control system that remotely pushes or pulls a catheter which is to be inserted into a lesion such as a blockage part or a stenosis part of the patient. The micro-robot includes a center shaft, a base part, a drill part, and head part. In order to be detachably attached to a projection of the catheter, a coupling hole is formed in a bottom, and the center shaft is provided in a direction vertical to a center of a floor opposite to the bottom. The base part includes an outer wall portion which is shorter than a length of the center shaft and is provided in direction vertical to a border of the floor. The drill part is rotatably coupled to the center shaft and generates a magnetic torque with an external rotating magnetic field in order for a drilling function to be performed, and is coupled to a first magnetic material. The head part is coupled to a distal end of the center shaft and has a diameter relatively larger than the distal end of the center shaft to limit movement of the drill part. The head part generates a magnetic torque with an external steering magnetic field in order for a steering function to be performed, and the head part includes a second magnetic material.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

The terms used herein are for the purpose of describing particular embodiments only and are not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Hereinafter, embodiments of the present invention will be described in detail with reference to the accompanying drawings.

Figure 1:
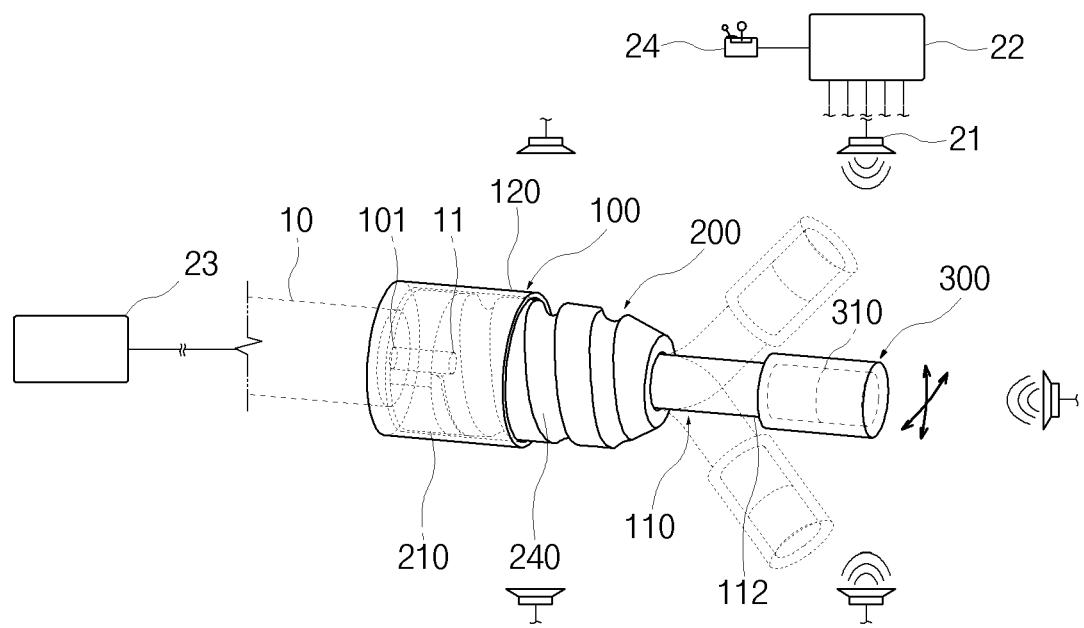
FIG. 1 is a perspective view illustrating a micro-robot detachably coupled to a catheter, according to an embodiment of the present invention.
Figure 2:
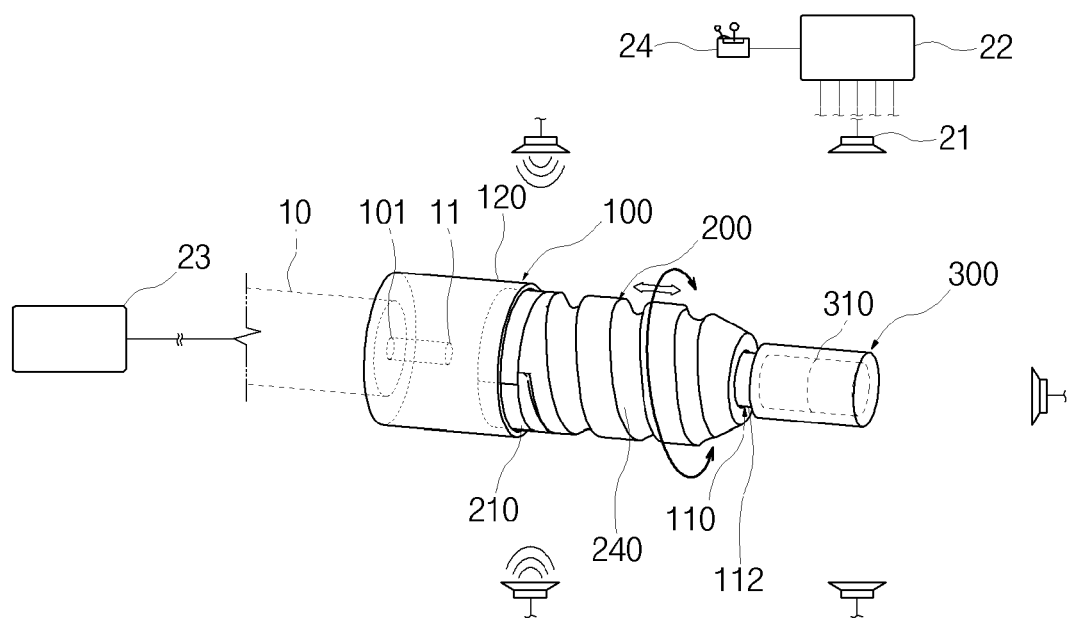
FIG. 2 is a perspective view illustrating a state where a drill part has been rotated and moved in the micro-robot detachably coupled to a catheter illustrated in FIG. 1.

FIG. 1 is a perspective view illustrating a catheter-attachable micro-robot according to an embodiment of the present invention. FIG. 2 is a perspective view illustrating a state where a drill part has been rotated and moved in the catheter-attachable micro-robot illustrated in FIG. 1.

Referring to FIG. 1, the catheter-attachable micro-robot according to an embodiment of the present invention may include a base part 100, a drill part 200, and a head part 300.

The catheter-attachable micro-robot according to an embodiment of the present invention may be applied to and used along with a magnetic field emitter 21 that is disposed in plurality outside a patient, a magnetic field control system 22 that controls an intensity of an external steering magnetic field or an external rotating magnetic field to provide the intensity-controlled external steering magnetic field or external rotating magnetic field to the magnetic field emitter 21, and a catheter control system 23 that remotely pushes or pulls a catheter which is to be inserted into a lesion such as a blockage part or a stenosis part of the patient. The magnetic field control system 22 may be further coupled to a remote controller 24 that may generate or control the external steering magnetic field or the external rotating magnetic field according to an intention of an operator.

Each of the magnetic field emitter 21 may denote a magnetic field radiator that emits an external steering magnetic field or an external rotating magnetic field. The magnetic field control system 22 or the catheter control system 23 may use configuration that is the same as or similar to that of a general blood vessel treatment robot system, and thus, its description may be omitted for clearly limiting and describing the present embodiment.

The catheter-attachable micro-robot according to an embodiment of the present invention may be detachably coupled to a guidewire (not shown) or a catheter 10 and used.

The catheter-attachable micro-robot according to an embodiment of the present invention may be a arteriosclerosis treatment medical apparatus that independently performs steering and tunneling with an external magnetic field supplied from a remote place such as the outside, and may be a means that realizes a minimum invasive method for increasing convenience of an operator and minimizing a treatment duration.

The catheter 10 may include a projection 11 that has a diameter relatively smaller than that of the catheter 10 and protrudes from a distal end of the catheter 10. Here, the projection 11 may be a portion corresponding to a guidewire lumen, or may denote a portion of the catheter 10.

Figure 5:
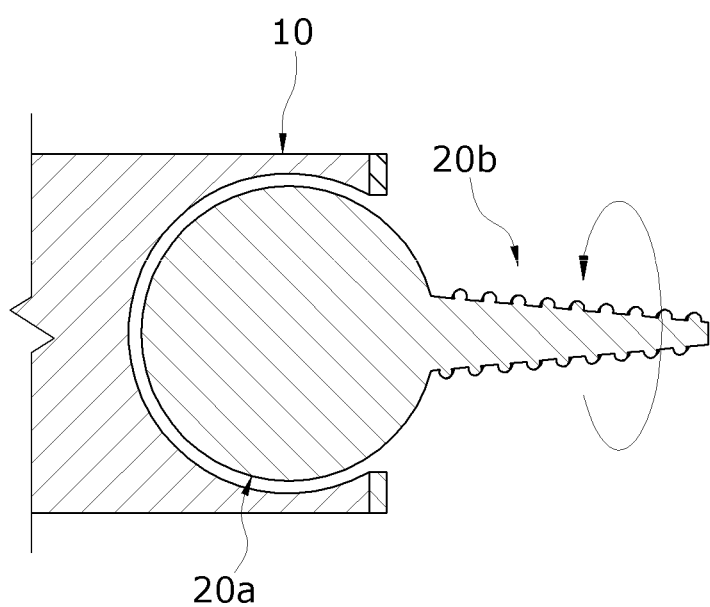
FIG. 5 is a side cross-sectional view illustrating a micro-robot integrated with catheter based on a ball socket joint according to an embodiment of the present invention.

According to another embodiment of the present invention illustrated in FIG. 5, a micro-robot integrated with a catheter may include a rotator micro-robot 400 that is disposed on one end of the catheter 10, based on a ball socket joint.

In this case, the rotator micro-robot 400 may rotate a rotatory member 420 which is coupled thereto according to steering based on a magnetic field, and thus, when opening a blockage lesion part, a desired part may be accurately opened through steering of the rotatory member 420.

The rotatory member 420, as illustrated in FIG. 5, may be provided in the form of spiral drill or propeller. This is for describing an embodiment of the present invention, and the scope of the present invention is not limited to the form.

That is, by using a drilling member coupled to the catheter 10, drilling may be performed in a predetermined axial direction, and moreover, steering may be performed when opening a lesion part, based on a ball socket joint.

A coupling hole 101 for the catheter 10 may be formed in a bottom of the base part 100 so that the base part 100 according to an embodiment of the present invention is detachably attached to the catheter 10 by forced-fitting to the projection 11 of the catheter 10. In the present embodiment, the coupling hole 101 may be formed to be forced-fitted to the projection 11.

According to a modification embodiment of the present invention, in a catheter (not shown) having a size smaller than a diameter of the robot according to the present embodiment, when the coupling hole 101 is small or largely formed based on a diameter of a small-size catheter, the small-size catheter may be coupled to the coupling hole 101 of the base part 100 through forced-fitting. Also, the catheter-attachable micro-robot according to an embodiment of the present invention may be directly attached to a distal end of the guidewire through the coupling hole 101. That is, a catheter having a small diameter may be very suitably coupled to the guidewire and used.

In the above-described embodiment, it has been described that the base part 100 is detachably attached to the catheter 10 through forced-fitting. However, the base part 100 may be coupled to the catheter 10 by a screw or a clamp.

In an embodiment of the present invention, the base part 100 may include a center shaft 110, which is provided in a direction vertical to a center of a floor opposite to a bottom, and an outer wall portion 120 that is provided in a direction vertical to a border of the floor to have a length shorter than that of the center shaft 110.

The base part 100 may be formed of one soft material selected from the group consisting of polydimethylsiloxane (PDMS) and flexible materials available for medical treatment. A material of the base part 100 may use a soft synthetic resin or a soft plastic material which is available within a body-friendly range, but is not limited thereto. For example, the soft material of the base part 100 may be a soft polymer material which does not cause a side effect in a human body and is good in antithrombotic.

The drill part 200 may have a cylindrical shape having a screw type.

The drill part 200 may have different internal diameters to be inserted in correspondence with the center shaft 110.

The drill part 200 may be formed of the same soft material as that of the base part 100, but is not limited thereto. In another embodiment, the drill part 200 may be formed of a hard material for enhancing durability of the drill part 200.

The drill part 200 may denote a component that rotates based on the base part 100. A portion of the drill part 200 may be disposed in the base part 100, and the other portion of the drill part 200 may be exposed to outside the base part 100. A first magnetic material 210 may be coupled to the drill part 200 so that a drilling function is performed with a magnetic torque generated by an external rotating magnetic field.

The first magnetic material 210 may be a permanent magnet. The first magnetic material 210 may have a structure similar to that of a motor rotor. That is, the first magnetic material 210 may denote a ring-shaped magnet having a plurality of N poles or S poles which are arranged in a circumference direction.

However, this is an example of the first magnetic material 210 for helping understanding of those skilled in the art, and the present invention is not limited to an example of including the first magnetic material 210 that is a permanent magnet. In another embodiment, the first magnetic material 210 may be replaced by a magnetic material which has a certain magnetization direction and is coated on the drill part 200.

An outer portion of the first magnetic material 210 may be coated by a soft polymer material which does not cause a side effect in a human body and is good in antithrombotic.

The head part 300 may be coupled to or integrated with the base part 100 through ultrasound bonding, thermal bonding, or adhering. For example, the head part 300 may be coupled to a distal end 114 of the center shaft 110 of the base part 100.

A second magnetic material 310 may be included in the head part 300. The head part 300 may generate a magnetic torque with an external steering magnetic field to perform a steering function. The second magnetic material 310 may denote a permanent magnet or a bar-type magnet.

However, this is an example of the second magnetic material 310 for helping understanding of those skilled in the art, and the present invention is not limited thereto. In another embodiment, the second magnetic material 310 disposed in the head part 300 may be replaced by a magnetic material which has a certain magnetization direction and is coated on the drill part 200.

In the head part 300, a protective film 320 surrounding the second magnetic material 310 may be formed of the same soft material as that of the based part 100.

The head part 300 may have a diameter relatively larger in size than the distal end of 114 of the center shaft 110 so that the drill part 200 moves along a shift extension direction of the center shaft 110, and then, a movement of the drill part 200 is limited within a predetermined movement stroke range.

A side border of the head part 300 except a portion coupled to the distal end 114 of the center shaft 110 may act as a stop jaw that prevents deviation or detachment of the drill part 200.

According to an embodiment of the present invention, by using the above-described flexible material or soft material, the steering function may be performed through bending or restoration based on only a magnetic torque having a relatively low level.

For example, the steering function may denote that when a portion of the drill part 200 is disposed in a space which is provided inward from the outer wall portion 120 of the base part 100, a coupling axis portion having a thinnest diameter in the center shaft 110 is bent or restored by an external steering magnetic field and a magnetic torque based on the second magnetic material 310 to change a position and a direction of the head part 300.

In an embodiment of the present invention, a tunneling function may be performed by the drill part 200. A rotation shaft of the drill part 200 may be the center shaft 110 applied to the steering function.

The drill part 200 having the first magnetic material 210 may rotate with an external rotating magnetic field.

Referring to FIG. 2, in order to perform the drilling function, the drill part 200 and a coupling axis portion of the center shaft 110 may be rotated by the external rotating magnetic field and a magnetic torque based on the first and second magnetic materials 210 and 310.

At this time, the drill part 200 may rotate or reversely rotate to generate a thrust or a reverse thrust and may move based on the thrust or the reverse thrust.

When the drill part 200 moves forward, a coupling axis portion 112 may be limited in steering, and thus, only the drill part 200 may rotate. Such a drilling function may be performed, thereby separating or removing a foreign material from a wall surface of a blood vessel of a patient.

The drill part 200 may be rotatably inserted into the center shaft 110 of the base part 100, but when the drill part 200 is disposed in fluid such as internal blood of a blood vessel, the drill part 200 acts as a screw or a propeller. Therefore, the drill part 200 may move in a forward direction with a thrust generated by rotation of the drill part 200, or may move in a backward direction with a reverse thrust generated by reverse direction of the drill part 200.

That is, the drilling function and the steering function may be independently performed so that when one of the drilling function and the steering function is being performed, the other function is not performed.

To provide an additional description, in order for the drilling function and the steering function to be independently performed, the drill part 200 may move along the shaft extension direction of the center shaft 110 of the base part 100.

Moreover, in another embodiment, the catheter 10 may be integratedly coupled to the magnetic micro-robot which is a ball member, based on a ball socket, and thus, when performing the drilling function, the catheter 10 may rotate while steering the rotatory member.

Figure 3:
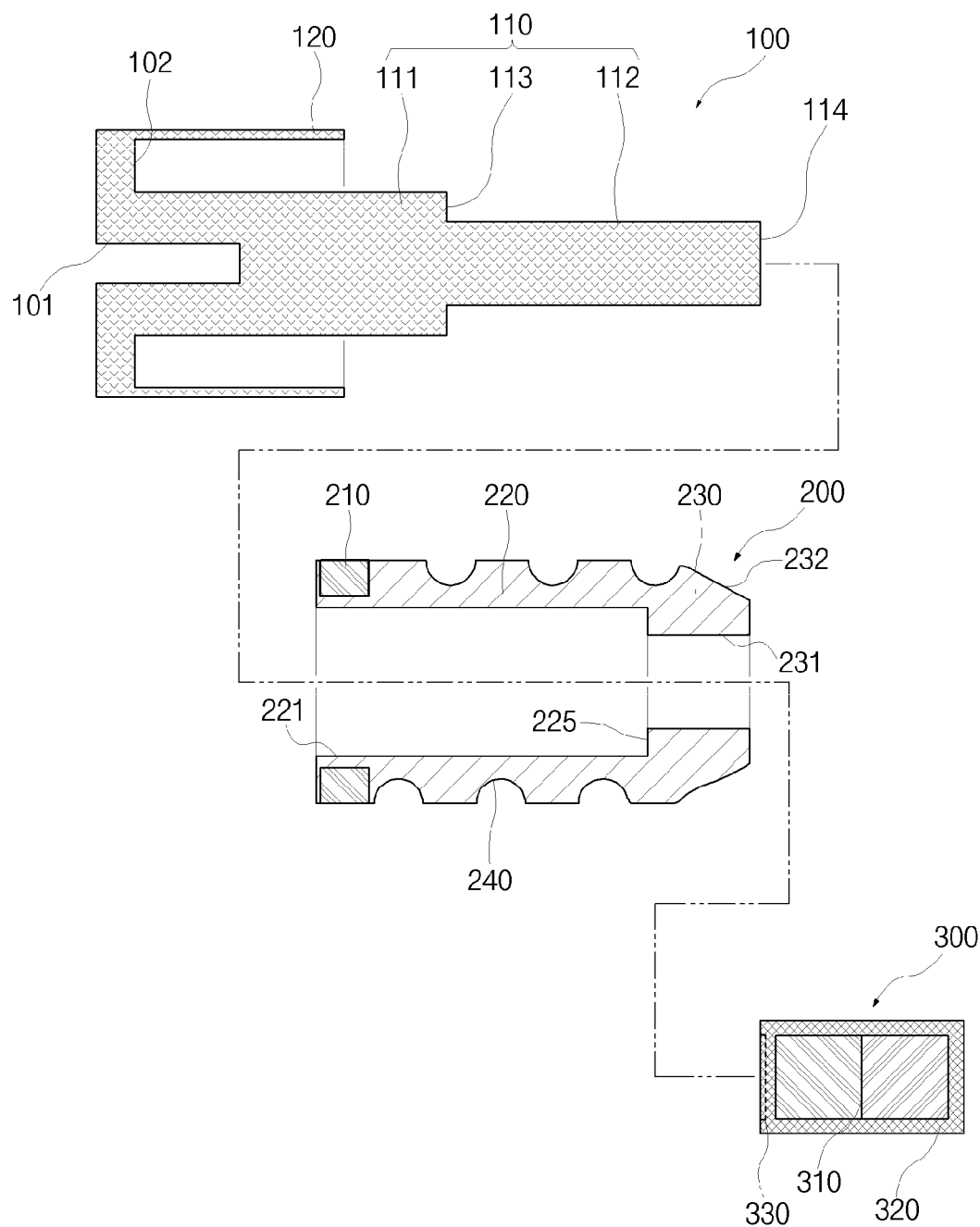
FIG. 3 is a cross-sectional view for describing a disassembly and assembly relationship of the micro-robot detachably coupled to a catheter illustrated in FIG. 1.
Figure 4:
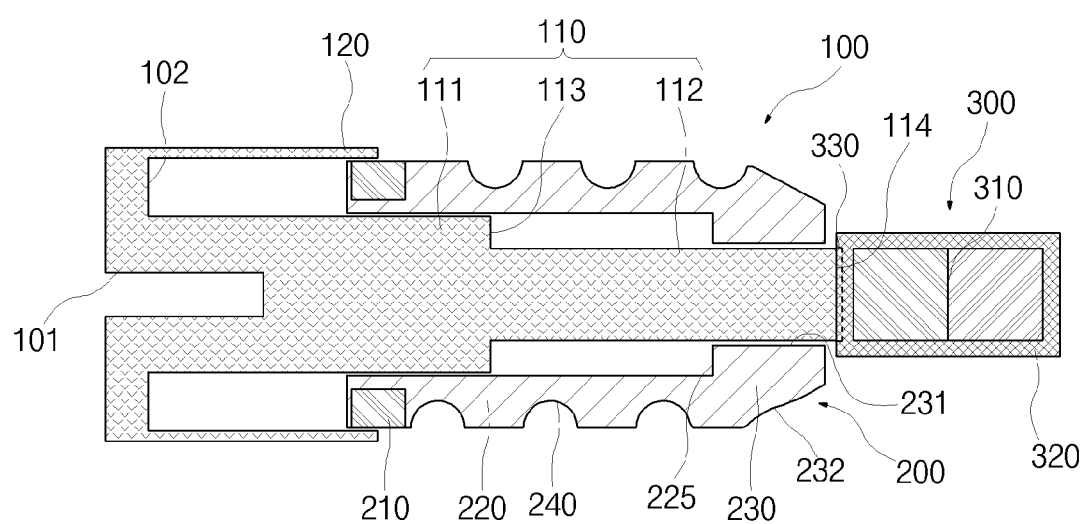
FIG. 4 is a cross-sectional view for describing a coupled state of the micro-robot detachably coupled to a catheter illustrated in FIG. 3.

FIG. 3 is a cross-sectional view for describing a disassembly and assembly relationship of the micro-robot detachably coupled to a catheter illustrated in FIG. 1. FIG. 4 is a cross-sectional view for describing a coupled state of the micro-robot detachably coupled to a catheter illustrated in FIG. 3.

The drill part 200, as described above, may be rotatably coupled to the center shaft 110 of the base part 100.

The center shaft 110 may include a basis axis portion 111 and a coupling axis portion 112.

The outer wall portion 120 may be closed by a floor 102, and a portion opposite to the floor 102 may be opened to accommodate a portion of the drill part 200.

The basis axis portion 111 may be integratedly coupled to a center of the floor 102 of the basis part 100. The basis axis may have a diameter smaller than an internal diameter of the outer wall portion 120 and a length relatively longer than that of the outer wall portion 120.

The coupling axis portion 112 may integratedly protrude from a top center of the basis axis portion 111 and may have a diameter relatively smaller than that of the basis axis portion 111.

The basis axis portion 111 and the coupling axis portion 112 may each be provided as a smooth outer circumference surface.

A corresponding portion of the drill part 200 which contacts the basis axis portion 111 and the coupling axis portion 112 may be provided as a smooth surface or a smooth inner circumference surface for reducing a friction. Therefore, the center shaft 110 and the drill part 200 may be rotatably coupled to each other to maintain only a gap equal to a tolerance.

Moreover, the center shaft 110 may include a first stepped surface 113 disposed between the basis axis portion 111 and the coupling axis portion 112. The first stepped surface 113 may be a friction surface or a contact surface corresponding to a second stepped surface 225 of the drill part 200.

The drill part 200 may include a tube-shaped body 220, having a wall thickness which enables the tube-shaped body 220 to be rotatably inserted between an inner circumference surface of the outer wall portion 120 and an outer circumference surface of the basis axis portion 111, and a tube-shaped body end portion 230 which is integratedly provided in a distal end of the tube-shaped body 220. An outer surface of the tube-shaped body 220 may also maintain a gap equal to a tolerance with respect to the outer wall portion 120.

Here, the body end portion 230 may include a stepped hole 231 small in size than a diameter of the basis axis portion 111. A diameter of the stepped hole 231 may be provided larger than an external diameter of the coupling axis portion 112 and smaller than an internal diameter of the tube-shaped body 230.

The body end portion 230 may be rotatably fitted to the coupling axis portion 112 through the stepped hole 231.

Moreover, the body end portion 230 may have a shape which is designed to efficiently perform the drilling function in a blood vessel or on a corn-shaped slope surface 232 that has a conical shape like a shape of a drill bit.

According to the drill part 200, an inner circumference surface 221 of the tube-shaped body 220 or an inner circumference surface of the stepped hole 231 of the body end portion 230 may be provided as a circumference surface having smooth roughness.

Moreover, a second stepped surface 225 contactable with the first stepped surface 113 may be provided between the inner circumference surface 221 of the tube-shaped body 220 and an inner circumference surface of the stepped hole 231.

Moreover, the drill part 200 may include a spiral groove portion 240 provided between an outer circumference surface of the tube-shaped body 220 and the slope surface 232 of the body end portion 230. The spiral groove portion 240 may denote a thread and a root of a screw.

Moreover, the head part 300 may be formed of the same material as that of the base part 100 through a molding process and may surround a surface of the second magnetic material 310.

The drill part 200 may be rotatably coupled to the center shaft 110, and then, the head part 300 may be integratedly bonded and connected or coupled to the distal end 114 of the coupling axis portion 112.

The head part 300 may further include a position determination groove 330 which is provided to be inserted into the distal end 114 of the coupling axis part 112 of the center shaft 110. The position determination groove 330 enables the coupling axis portion 112 to be easily and accurately assembled with the head part 300.

The head part 300 may be provided in a cylindrical shape. A shape of the head part 300 may be modified into and provided as one shape of a hemispherical shape, a spherical shape, a capsular shape, and an elliptic shape, except for a portion bonded to the distal end 114 of the coupling axis portion 112. Also, the head part 300 may be provided in a lanceted shape for maximizing performance of passing through an internal space of a blood vessel, and since an appearance of the head part 300 is provided in various shapes depending on the use or function of the head part 300, the appearance of the head part 300 is not limited to a specific shape.

Moreover, the head part 300 may be manufactured in a detachable type, and then, may be coupled to the center shaft 110. In a case of using three-dimensional (3D) printing technology, the head part 300 may be an output material having a state where the head part 300 is integrated with the base part 100 in a state where the drill part 200 is rotatably coupled o the center shaft 110, based on a 3D printer.

Hereinafter, an operation relationship of the catheter-attachable micro-robot according to an embodiment of the present invention.

Referring to FIG. 1, while performing a medical operation based on the catheter 10, the drill part 200 may be moved toward the catheter 10 by pressure of fluid such as blood in a blood vessel, and may be disposed in a space provided inward from the outer wall portion 120.

In this case, the center shaft 110 may be exposed to outside the drill part 200.

In this state, the magnetic field emitter 21 may emit an external steering magnetic field for controlling the direction, position, or deflection of the head part 300, namely, the steering function.

The head part 300 may be supplied with a magnetic torque based on the external steering magnetic field through the second magnetic material 310 thereof. In this case, since the coupling axis portion 112 of the center shaft 110 includes a soft material and is relatively smaller in diameter than the basis axis portion 111, the coupling axis portion 112 may be the lowest in bending rigidity, and since the base part 100 is supported by the catheter, the coupling axis portion 112 is bent.

For example, in the center shaft 110, a diameter of the coupling axis portion 112 may be 400 μm, a diameter of the basis axis portion 111 may be 700 μm, and an external diameter of the outer wall portion 120 may be 1,200 μm. Therefore, bending easily occurs depending on a diameter or an external diameter with respect to the coupling axis portion 112 which is relatively low in bending rigidity.

Therefore, a direction of the head part 300 is easily changed to a target position or a target direction according to control based on the external steering magnetic field, and thus, steering is quickly performed.

The screw-type drill part 200 may be moved by the above-described thrust as in FIG. 2, and the drill part 200 may surround the coupling axis portion 112.

As described above, bending rigidity increases to a degree to which the coupling axis portion 112 is not bent through the drill part 200. Therefore, it is unable to perform steering with only a magnetic torque which is generated for steering, but the drill part 200 may perform the drilling function while smoothly rotating with respect to the coupling axis portion 112 or the basis axis portion 111 (see FIG. 3) which is rectilinearly spread.

Particularly, the drill part 200 may be disposed in blood or fluid in a blood vessel of a patient and may be rotated by a magnetic torque based on an external rotating magnetic field. At this time, the spiral groove portion 240 may change the amount of exercise of the fluid, thereby generating a thrust for the drilling function.

When the drill part 200 reversely rotates or stops, the drill part 200 may restore to a state illustrated in FIG. 1 and may be put in a state which enables the steering function to be performed.

Hereinafter, a micro-robot integrated with catheter based on a ball socket joint according to another embodiment of the present invention will be described with reference to FIGS. 5 to 10.

Referring to FIG. 5, a rotary part disposed in one end of a catheter or a guidewire 10 may include a ball member 20a and a rotary member 20b.

A whole portion or a portion of the rotary part 20 may be formed of a magnetic material or may be coated with a magnetic material. Therefore, steering and rotation of the rotary part 20 may be performed by a magnetic field emitter disposed outside a patient.

According to an embodiment of the present invention, the rotary part 20 may be disposed based on a ball socket joint, and steering and rotation of the rotary part 20 may be performed based on a degree of freedom of 360 degrees.

Figure 6:
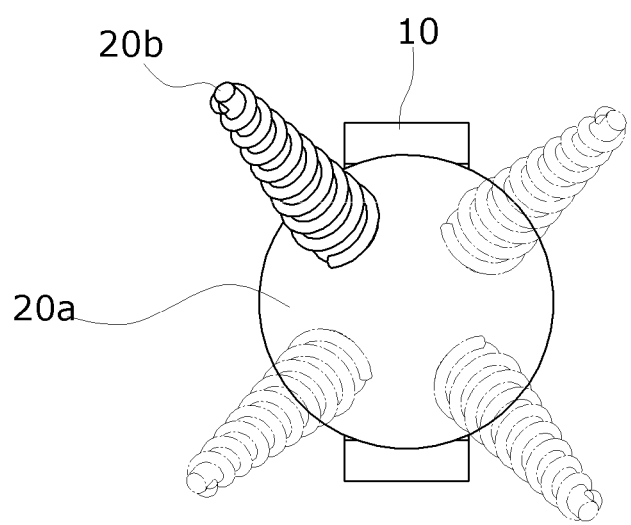
FIG. 6 is a front view illustrating a micro-robot integrated with catheter based on a ball socket joint according to an embodiment of the present invention.

FIG. 6 is a front view illustrating a micro-robot integrated with catheter based on a ball socket joint according to an embodiment of the present invention.

As illustrated in FIG. 6, according to an embodiment of the present invention, fine steering of the rotary part 20 (20a and 20b) may be performed by a magnetic field with a degree of freedom of 360 degrees.

Figure 7:
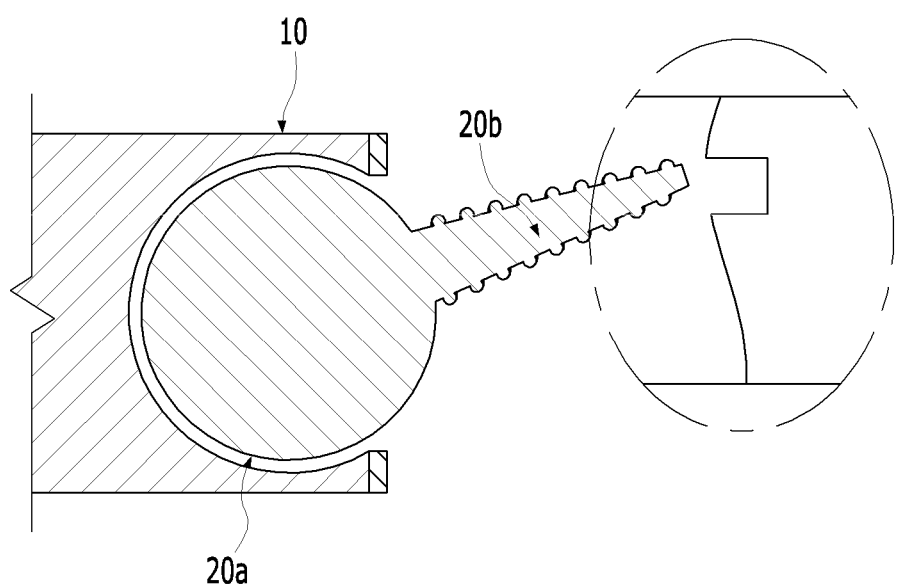
FIG. 7 is a conceptual view illustrating fine steering of a lesion opening position of a micro-robot integrated with catheter based on a ball socket joint according to another embodiment of the present invention.

Therefore, unlike the related art where drilling is performed for a center portion of a lesion in opening the lesion, according to an embodiment of the present invention illustrated in FIG. 7, an accurate region of a blockage lesion may be opened by performing fine steering on a gap (a portion which is to be drilled) of the blockage lesion with the rotary member 20b having a spiral drill shape, based on a ball socket joint.

An embodiment of the present invention is not limited to that the rotary member 20b rotates dependent on the ball member 20a.

That is, a whole portion or a portion of the rotary part 20 (including the ball member 20a and the rotary member) according to an embodiment of the present invention may be formed of a magnetic material or may be coated with a magnetic material. Therefore, a force and a torque for opening a lesion is secured by driving the rotary part 20 with a magnetic field, and the lesion is opened through fine steering by using a degree of freedom of 360 degrees.

Figure 8:
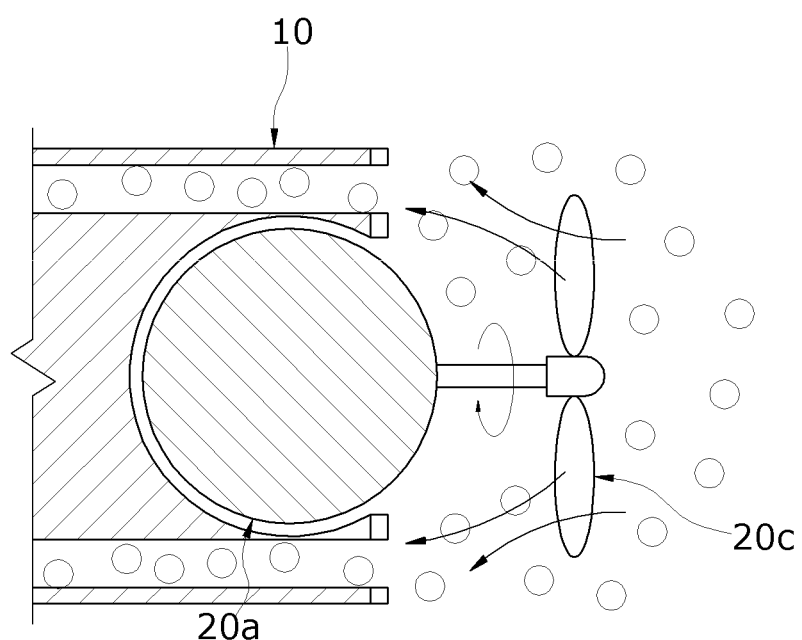
FIG. 8 is a conceptual view illustrating a residue suction operation of a micro-robot integrated with catheter based on a ball socket joint according to another embodiment of the present invention.

FIG. 8 is a conceptual view illustrating a residue suction operation of a micro-robot integrated with catheter based on a ball socket joint according to another embodiment of the present invention.

A rotary member 20c of a rotary part 20 according to an embodiment of the present invention may be implemented in a propeller shape and may rotate to suck residues which occur in opening a blockage lesion.

A flow path may be formed in one end of a catheter 10. The sucked residues may be collected through the flow path and processed.

Moreover, the rotary member 20c may adjust a flow velocity at which residues which occur in opening a blockage lesion is sucked.

Figure 9:
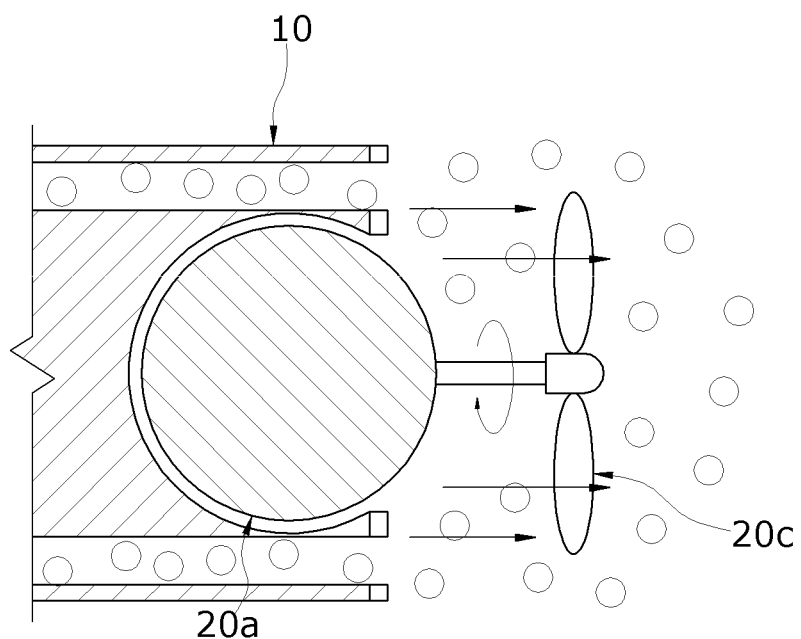
FIG. 9 is a conceptual view illustrating a drug transfer operation of a micro-robot integrated with catheter based on a ball socket joint according to another embodiment of the present invention.

FIG. 9 is a conceptual view illustrating a drug transfer operation of a micro-robot integrated with catheter based on a ball socket joint according to another embodiment of the present invention. The rotary member 20c may be implemented in a propeller shape and may transfer drug, which is discharged from a drug transfer module included in the catheter 10 according to rotation of the rotary member 20c, to a lesion.

In this case, the rotary member 20c may adjust a flow velocity of drug which is discharged through the flow path formed in the one end of the catheter 10 according to rotation of the rotary member 20c.

Figure 10A:
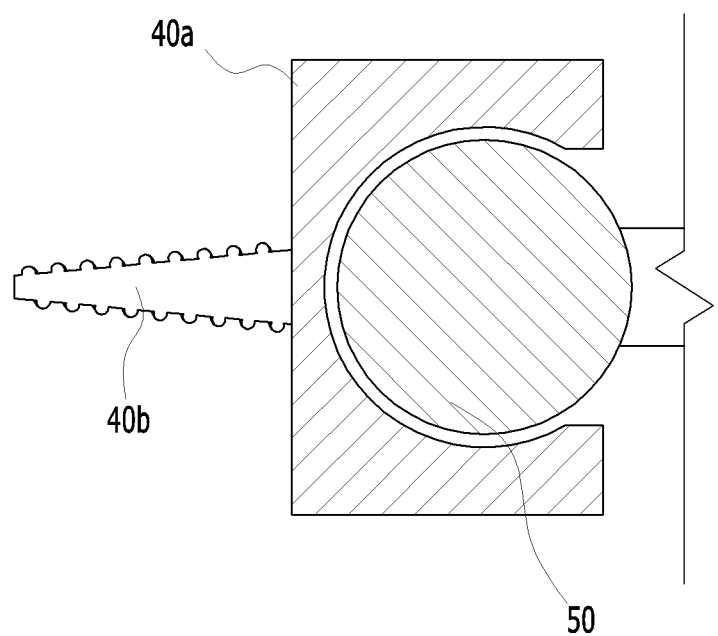
FIG. 10A and FIG. 10B are side cross-sectional views illustrating a micro-robot integrated with catheter based on a ball socket joint according to another embodiment of the present invention.
Figure 10B:
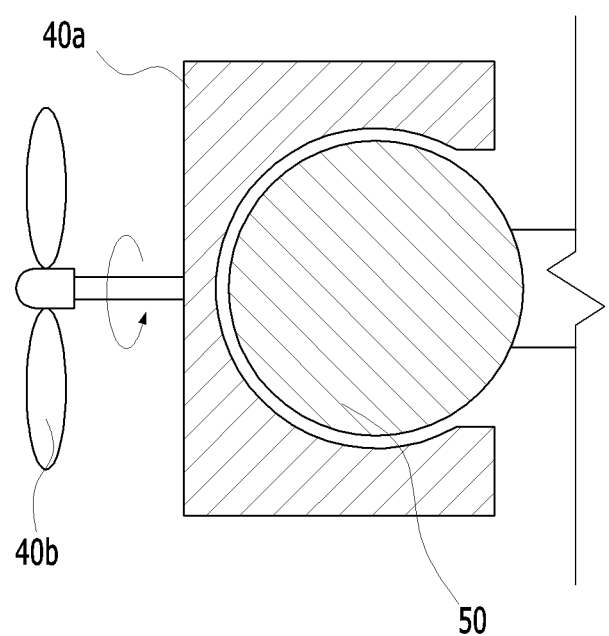

FIG. 10A and FIG. 10B are side cross-sectional views illustrating a micro-robot integrated with catheter based on a ball socket joint according to another embodiment of the present invention.

According to another embodiment of the present invention, in the micro-robot integrated with catheter based on a ball socket joint, a rotary part 40 including a ball member 50 may be disposed in a front end of the micro-robot. A whole portion or a portion of the rotary 40 may be formed of a magnetic material or may be coated with a magnetic material. The rotary part 40 may finely steer and rotate a plurality of rotary members 40b and 40c having a spiral drill shape or a propeller shape by controlling an external magnetic field.

A micro-robot detachably coupled to a catheter according to another embodiment of the present invention may be coupled to and disposed in an opening part of a catheter and may perform fine steering by using an output magnetic field in an opening operation using the catheter.

Figure 11:
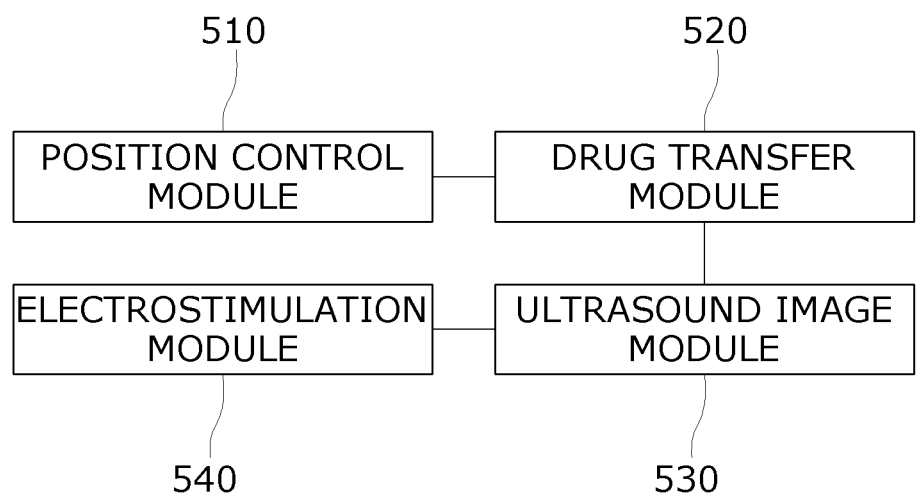
FIG. 11 is a block diagram illustrating an internal module of a micro-robot coupled to a catheter, according to another embodiment of the present invention.

In this case, an internal module of the micro-robot may be as illustrated in FIG. 11. In opening a cardiovascular blockage lesion, a position control module 510 may perform fine steering so that movement is made in an x-axis direction and a y-axis direction and an angle is controlled with respect to a z axis.

Due to the fine steering, a local part may be accurately opened, and thus, a risk of injury and infection is minimized in opening a lesion.

When the micro-robot enters a local part through the fine steering, the micro-robot may perform a unique function thereof by using a drug transfer module 520, an ultrasound image module 530, and an electrostimulation module 540.

As described above, in the micro-robot coupled to the catheter according to the embodiments of the present invention, since the base part is formed of a flexible material and the center shaft of the base part coupled to the drill part is configured with the basis axis portion and the coupling axis portion, the coupling axis portion having a relatively thinnest diameter is easily bent with only an intensity (for example, 10 mT to 20 mT) of an external magnetic field having a relatively low level, and thus, a sensitive and are steering function is performed.

That is, in the micro-robot coupled to the catheter according to an embodiment of the present invention, a magnetic material having a relatively small size may be mounted on the head part coupled to the distal end of the coupling axis portion by using an external magnetic field for bending only the coupling axis portion in the base part coupled to the projection formed in the distal end of the catheter, and thus, a catheter which is relatively far thinner may be applied.

Moreover, in the micro-robot coupled to the catheter according to an embodiment of the present invention, since the steering function and the drilling function are independently performed, a time is relatively further shortened than a treatment performed by a related art catheter, and thus, a time for which a patient and a doctor are exposed to radiation is reduced.

Moreover, in the micro-robot coupled to the catheter according to an embodiment of the present invention, since the coupling hole is formed in the bottom of the base part, the micro-robot may be detachably attached to the catheter by being forced-fitted to the projection formed in the distal end of the catheter, and thus, maintenance and repair are easily performed.

Moreover, according to an embodiment of the present invention, an operator or a doctor may secure a path in a blood vessel by using the guidewire, and then may perform a medical procedure by using one robot without additionally performing a tunneling operation of inserting the catheter. Accordingly, a surgery such as chronic total occlusion or the like is quickly performed, and thus, a side effect is reduced.

In the micro-robot coupled to the catheter according to another embodiment of the present invention, by using the magnetic micro-robot integratedly coupled to one end of the catheter, axis-direction movement and axis-direction angle control may be performed through fine steering when opening a lesion. Also, if the magnetic micro-robot is integrated with the catheter based on the ball socket, the catheter is smoothly inserted into a lesion part by steering and rotating the rotary member.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A micro-robot coupled to a catheter or a guidewire, the micro-robot comprising:
a base part detachably attached to the catheter or the guidewire, the base part including a center shaft;
a drill part rotatably coupled to the center shaft to generate a first magnetic torque based on an external rotating magnetic field to perform a drilling function; and
a head part coupled to a distal end of the center shaft to generate a second magnetic torque based on an external steering magnetic field to perform a steering function, the head part having a diameter relatively larger than the distal end of the center shaft.

2. The micro-robot of claim 1, wherein
the base part is detachably attached to a projection provided in an end portion of the catheter or the guidewire, and
a first magnetic material is coupled to the drill part or coated on an outer portion of the drill part, and a second magnetic material is included in the head part or coated on an outer portion of the head part.

3. The micro-robot of claim 2, wherein the base part is formed of one soft material selected from a group consisting of polydimethylsiloxane (PDMS) or flexible materials available for medical treatment.

4. The micro-robot of claim 3, wherein
the base part comprises:
a coupling hole provided in a bottom of the base part to be detachably attached to the projection provided in the end portion of the catheter or the guidewire through forced-fitting; and
an outer wall portion, the outer wall portion being shorter in length than the center shaft,
the center shaft is provided in a direction vertical to a center of a floor opposite to the bottom, and
the outer wall portion is provided in a direction vertical to a border of the floor.

5. The micro-robot of claim 4, wherein the center shaft comprises:
a basis axis portion integratedly coupled to the center of the floor, the basis axis portion having a diameter smaller than an internal diameter of the outer wall portion and having a length relatively longer than a length of the outer wall portion; and
a coupling axis portion integratedly protruding from a top center of the basis axis portion, the coupling axis portion having a diameter relatively smaller than the diameter of the basis axis portion.

6. The micro-robot of claim 5, wherein
the head part is formed of the same material as a material of the base part to surround a surface of the second magnetic material, and
the drill part is rotatably assembled to the center shaft, and the head part is integratedly bonded and coupled to a distal end of the coupling axis portion.

7. The micro-robot of claim 5, wherein
the drill part comprises:
a tube-shaped body having a wall thickness which enables the tube-shaped body to be rotatably inserted between an inner circumference surface of the outer wall portion and an outer circumference surface of the basis axis portion;
a body end portion integratedly provided in a distal end of the tube-shaped body, the body end portion including a stepped hole smaller than the diameter of the basis axis portion and a slope outer circumference surface that is rotatably assembled to the coupling axis portion through the stepped hole and has a conical shape similar to a shape of a drill bit; and
a spiral groove portion provided in an outer circumference surface of the tube-shaped body and in a slope surface of the body end portion,
the drill part is placed in blood or fluid in a blood vessel of a patient to rotate by the first magnetic torque based on the external rotating magnetic field, and
the spiral groove portion changes an amount of exercise of the fluid to generate a thrust for the drilling function of the drill part.

8. The micro-robot of claim 6, wherein the drill part is formed of a hard material or the same soft material as the material of the base part.

9. The micro-robot of claim 7, wherein a circumference surface of the drill part corresponds to an inner circumference surface of the tube-shaped body or an inner circumference surface of the stepped hole of the body end portion.

10. The micro-robot of claim 9, wherein when a portion of the drill part is disposed in a space which is provided inward from the outer wall portion, the coupling axis portion of the center shaft is bent by the second magnetic torque based on the second magnetic material and the external steering magnetic field to perform the steering function of changing a positon and a direction of the head part.

11. The micro-robot of claim 10, wherein
the drill part is rotated or reversely rotated by the external rotating magnetic field and the first and second magnetic torques based on the first and second magnetic materials, in association with the coupling axis portion to generate a thrust or a reverse thrust,
as the drill part is move based on the thrust or the reverse thrust, rotating of the coupling axis portion is limited by the drill part, and
the drill part is rotated to separate or remove a foreign material from a wall surface of the blood vessel of the patient.

12. The micro-robot of claim 11, wherein the drilling function and the steering function are independently performed so that when one of the drilling function and the steering function is being performed, other one function is not performed.

\* \* \* \* \*